US010702423B1

(12) United States Patent
Krasnow et al.

(10) Patent No.: US 10,702,423 B1
(45) Date of Patent: Jul. 7, 2020

(54) ULTRASOUND COMMUNICATIONS FOR LOW-POWER BIOSENSOR APPLICATIONS

(71) Applicant: Verily Life Sciences LLC, South San Francisco, CA (US)

(72) Inventors: Benjamin Krasnow, Redwood City, CA (US); Eric Peeters, Redwood City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 353 days.

(21) Appl. No.: 15/872,107

(22) Filed: Jan. 16, 2018

Related U.S. Application Data

(60) Provisional application No. 62/448,797, filed on Jan. 20, 2017.

(51) Int. Cl.
*A61F 13/42* (2006.01)
*H04B 11/00* (2006.01)

(52) U.S. Cl.
CPC ............. *A61F 13/42* (2013.01); *H04B 11/00* (2013.01); *A61F 2013/424* (2013.01)

(58) Field of Classification Search
CPC ..... A61F 13/42; A61F 2013/424; H04B 11/00
See application file for complete search history.

(56) References Cited

U.S. PATENT DOCUMENTS

| 10,028,865 B2 * | 7/2018 | Krasnow | G01N 27/121 |
| 2017/0354546 A1 * | 12/2017 | Krasnow | A61F 13/42 |
| 2018/0193567 A1 * | 7/2018 | Schleicher | A61M 5/344 |
| 2019/0262543 A1 * | 8/2019 | Reich | A61M 5/31546 |

FOREIGN PATENT DOCUMENTS

| EP | 3469346 A1 * | 4/2019 | H01M 4/06 |
| WO | WO-2017218066 A1 * | 12/2017 | H01M 6/32 |

* cited by examiner

*Primary Examiner* — Daniel Pihulic
(74) *Attorney, Agent, or Firm* — Kilpatrick Townsend & Stockton LLP

(57) ABSTRACT

The present disclosure relates to systems and methods for low-power, data transmission using ultrasound signals. In one implementation, a data transmission system includes an ultrasound transducer configured to generate ultrasound signals in response to power supplied from a power source, and a mechanical ultrasound amplifier coupled to the ultrasound transducer, the ultrasound amplifier having a substrate adapted to function as a soundboard to amplify the ultrasound signals. The range of the data transmission system may be increased with a relay system. The relay system may include one or more detectors and one or more repeaters.

20 Claims, 8 Drawing Sheets

ULTRASOUND COMMUNICATIONS FOR LOW-POWER BIOSENSOR APPLICATIONS

CROSS-REFERENCE TO RELATED APPLICATIONS

This application claims priority to U.S. Provisional Application No. 62/448,797, filed Jan. 20, 2017, entitled "Ultrasound Communications for Low-Power Biosensor Applications," which is incorporated herein by reference in its entirety.

FIELD

The present disclosure relates generally to the field of data communications and low-power data transmission systems. More specifically, and without limitation, this disclosure relates to systems and methods for wireless communications through the use of an ultrasound transducer coupled to a substrate that functions like a soundboard. The ultrasound transducer may be used in various applications, including a biosensor application for a personal hygiene product where moisture detection signals are transmitted to an external monitoring device.

BACKGROUND

To enable data communications from one device to another, data may be collected and converted into a signal for transmission. In some applications, wireless transmissions between devices may be achieved using electrical or electromagnetic signals. One of the most common forms of a wireless transmission signal is a radio frequency (RF) signal. However, the power requirements for RF transmissions can impede attempts to provide miniaturized and/or energy efficient devices. In addition, the high cost of RF transmitters impedes their cost-effective use in disposable products.

Examples of products that could benefit from a low cost and energy efficient, data communications solution include personal hygiene products. With such products, it may be desirable to transmit sensor data and/or other signals to an external device, such as a monitor. Because a personal hygiene product may be disposable and have a limited power source, there is a need for a low cost and power efficient, biosensor solution. Furthermore, the data transmitter must have a sufficient range so that an external device is capable of receiving the signals transmitted from the product. Also, in such applications, the sensor, data transmitter, and other circuit components must be sufficiently small to provide design flexibility and enable optimized placement within the product.

SUMMARY

In view of the foregoing, embodiments of the present disclosure provide a low cost and power efficient, data communications solution for personal hygiene products and other applications. In accordance with some embodiments, a transducer is provided for transmitting ultrasound signals to one or more external devices. Due to its low cost and power efficiency, the ultrasound transducer can be incorporated into disposable hygiene products, such as a diaper, liner, bed pad, or tampon. In addition, the transmission range of the ultrasound transducer can be enhanced by coupling the transducer to a substrate that functions like a soundboard to amplify the ultrasound signals.

According to an exemplary embodiment of the present disclosure, a data transmission system is described. The system may include a power source, a transducer that generates ultrasound signals in response to power supplied from the power source, and a substrate that is coupled to the transducer. The substrate may be adapted to function as a soundboard for amplifying the ultrasound signals generated by the transducer.

According to a yet further exemplary embodiment of the present disclosure, a data transmission system for use in a personal hygiene product is described. The system may include a power source, a sensor that detects a moisture level in an absorption area of the personal hygiene product, a transducer that generates ultrasound signals in response to power supplied from the power source, and a substrate that is coupled to the transducer. The substrate may be adapted to function as a soundboard for amplifying the ultrasound signals generated by the transducer.

According to a yet further exemplary embodiment of the present disclosure, a data transmission method is described. The method includes the steps of providing a power source, applying power from the power source to a transducer, generating ultrasound signals with the transducer in response to supplying power to the transducer, and amplifying the ultrasound signals using the substrate.

Certain embodiments of the present disclosure relate to systems and methods that are adapted to relaying a data transmission from an ultrasound transducer. The range of an ultrasound transducer is generally shorter than that of traditional technologies like RF transmitters. One solution is to introduce a relay system that detects the ultrasound signal and repeats the detected signal.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the disclosed principles. In the drawings:

FIG. 4b is a schematic representation of an example of the layers included in absorption area 413 of FIG. 4a.

DETAILED DESCRIPTION

Figure 1:
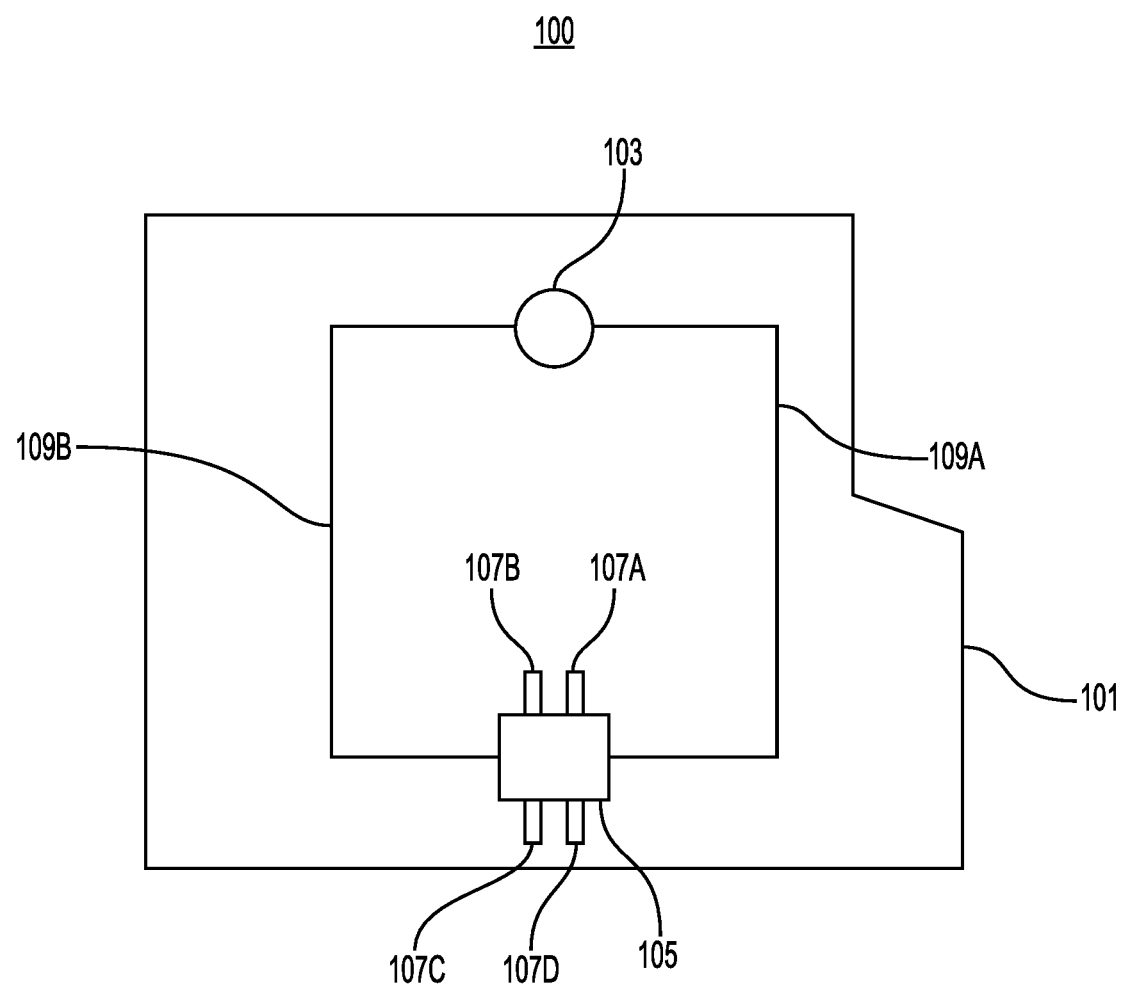
FIG. 1 is a schematic representation of an exemplary ultrasound communications system, according to embodiments of the present disclosure.

The disclosed embodiments relate to systems and methods for wirelessly transmitting data with an ultrasound transducer. Advantageously, the exemplary embodiments may provide a low power and cost-effective solution to transmit data, including sensor data. Embodiments of the present disclosure may be implemented as part of a miniaturized transmitter or electronics component set. Furthermore, embodiments of the present disclosure include various applications, including a biosensor application for a personal hygiene product, such as a diaper, liner, bed pad, or tampon. Applications consistent with the present disclosure also encompass customized electronic devices and products with wireless transmission functions.

According to an aspect of the present disclosure, a data transmission system is provided. The data transmission system may include a power source. In some embodiments, the power source may be voltage source activated by an environmental variable, for example moisture or temperature. In some embodiments, the power source may be a small battery.

According to another aspect of the present disclosure, the data transmission system may include a controller. By way of example, the controller may be a microcontroller unit adapted to produce an electric signal in response to an environmental change. In other embodiments, the controller may include one or more transistors adapted to produce an electric signal given an environmental change or level.

According to a further aspect of the present disclosure, the data transmission system may include a transducer. In some embodiments, the transducer may be driven at self-resonance and may generate ultrasound signals. In other embodiments, a controller may drive the transducer at a resonance frequency.

Consistent with other aspects of the present disclosure, the data transmission system may include a capacitive transducer that is capable of generating ultrasound signals. In such arrangements, the cost of the transducer may be reduced if a capacitive resistor is used.

According to a still further aspect of the present disclosure, the data transmission system may include a substrate. In some embodiments, the substrate may be adapted to function as a soundboard to amplify signals generated by the ultrasound transducer. Preferably, the substrate may include a hard or rigid material with resonant properties. In certain aspects, the hard material may include, for example, materials used in traditional soundboards, such as hardwoods; polyethylene terephthalate or other plastics; or any combination thereof. In other aspects, the substrate may be formed with or as part of a printed circuit board. In such cases, the material may include, for example, materials used in traditional printed circuit boards, such as fiberglass, epoxy, or polyimide. Other possible materials include, for example, silicon, silicon dioxide, aluminum oxide, sapphire, germanium, gallium arsenide, alloys including at least silicon and germanium, or indium phosphide. Advantageously, the power required to drive the transducer may be reduced if the substrate is coupled to the transducer and functions as a soundboard to amplify the ultrasound signals generated by the transducer.

In some embodiments, the substrate may be selected or constructed to provide a resonant frequency that matches the resonant frequency of the transducer. In certain aspects, the geometry of the substrate may be varied or selected in order to adapt its resonant frequency. In other aspects, the composition of the substrate may be varied or selected in order to adapt its resonant frequency. In other aspects, a combination of these techniques, and/or other known techniques, may be used.

In some embodiments, the substrate may include a flexible material. In certain aspects, the flexible material may include, for example, materials used in traditional flexible plastic substrates, such as polyimide, PEEK, or transparent conductive polyester; materials used in traditional flexible printed circuit boards, such as polyimide foil, polyimide-fluoropolymer composite foil, or other similar materials; or any combination thereof. Advantageously, the power required to drive the transducer may be reduced if the resonant frequency of the substrate matches the resonant frequency of the transducer.

Consistent with embodiments of the present disclosure, the substrate may be coupled to the transducer. In certain aspects, the data transmission system may include solder pads that couple the transducer to the substrate. In other embodiments, the transducer may be embedded in the substrate. Advantageously, the substrate may act to resonant the signals from the transducer and increase the transmission range thereof when coupled to the transducer.

According to an aspect of the present disclosure, the data transmission system may include a relay system. The relay system may include one or more detectors and/or repeater devices. Advantageously, the relay system may increase the range of the transmitted signal.

In certain aspects, the relay system may include one or more detectors. In some embodiments, a detector may include a microphone. Advantageously, conventional mobile phone microphones may be usable as the detector.

In certain aspects, the detector may include a transceiver. For example, a piezoelectric transceiver may include a piezoelectric ceramic, such as PZT ceramic, or a single-crystal material, such as gallium phosphate, quartz, or tourmaline. Advantageously, the transceiver may function both as a detector and as a repeater.

In certain aspects, the relay system may include one or more repeaters. In some embodiments, a repeater may include an ultrasound transmitter. In other embodiments, a repeater may include an RF transmitter. Advantageously, conventional mobile phones are equipped with RF transmitters and may be used as a repeater.

FIG. 1 is a schematic representation of an exemplary ultrasound communications system 100, consistent with embodiments of the present disclosure. As shown in the example of FIG. 1, system 100 includes a power source 103 and a substrate 101. Power source 103 may include a battery or other voltage source. Communications system 100 also includes a transducer 105 that generates ultrasound signals. Depending on the layout, geometry, and/or application of system 100, substrate 101 may provide one or more electrical connections, including between power source 103 and transducer 105. In the example of FIG. 1, power source 103 is connected to transducer 105 by electrically conductive wires or traces 109a and 109b. In some embodiments, substrate 101 is a printed circuit board and supports other components in addition to those illustrated in FIG. 1.

Depending on the layout, geometry, and/or application of system 100, transducer 105 may be coupled to substrate 101. In the example of FIG. 1, transducer 105 is coupled to substrate 101 by one or more solder pads, e.g., pads 107a, 107b, 107c, and 107d. As will be appreciated from this disclosure, system 100 may further include other components, such as capacitors, transistors, transducers, memory, controllers, sensors, switches, etc. (not shown in FIG. 1). Such components may also be coupled to substrate 101 and connected to one another by electrically conductive wires or traces 109*a* and 109*b*.

In some embodiments, power source 103 may include a voltage source activated by an environmental variable, for example a moisture or temperature level. In such arrangements, a moisture or temperature sensor may detect an environmental level and cause power source 103 to activate. For example, source 103 may provide an A/C current upon activation. Preferably, the frequency of the A/C current may match a resonant frequency of transducer 105. Advantageously, this may remove the need for any controller to activate the transducer 105.

In some embodiments, transducer 105 may be driven at self-resonance. At self-resonance, the impedance of transducer 105 may be at a minimum because the imaginary portions of the impedance may cancel and the impedance may therefore be equal only to real resistance. Advantageously, this may reduce the power required from power source 103 to drive the transducer 105.

In some embodiments, transducer 105 may include a capacitor. Advantageously, the use of a capacitive transducer may reduce the cost of the transducer and/or the system. For example, a surface-mount capacitor may cost approximately ten times less than a Bluetooth® transmitter.

As described herein and shown in the example of FIG. 1, transducer 105 may be coupled to substrate 101 with one or more solder pads 107*a*, 107*b*, 107*c*, and 107*d*. Other coupling arrangements are possible. For example, transducer 105 may be coupled to substrate 101 with any number of solder pads. It is also possible to couple transducer 105 to substrate 101 with through-hole technology rather than surface-mount technology. It is further possible to form transducer 105 directly on substrate 101 or to embed transducer 105 on substrate 101.

In data transmission system 100, power source 103 may activate due to an environmental variable or level. For example, as noted above, the variable may be a moisture level or a temperature level. In such arrangements, power source 103 may activate at a pre-determined environmental variable or level supply power to transducer 105. Power source 103 may be connected to transducer 105 by electrical connections 109*a* and 109*b*. Power source 103 may drive transducer 105 at a resonance frequency.

Figure 2:
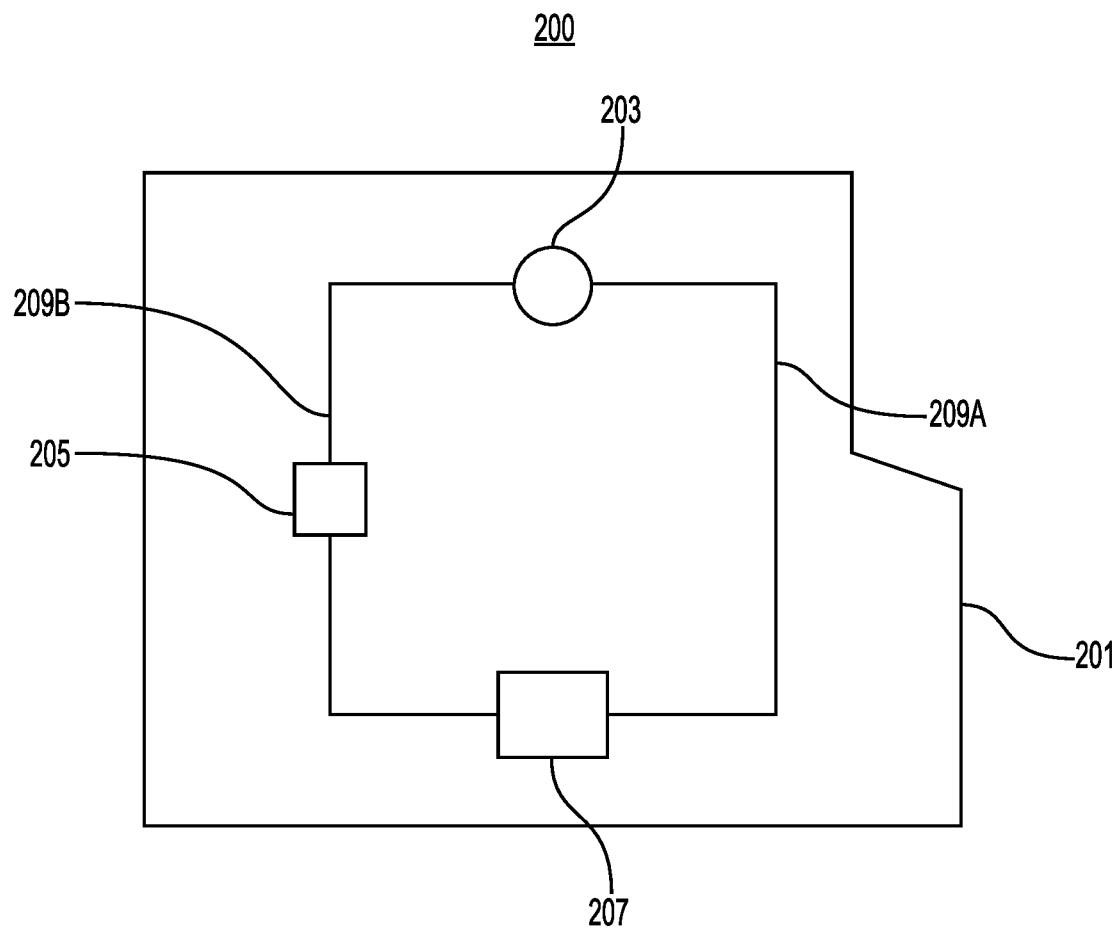
FIG. 2 is a schematic representation of another exemplary ultrasound communications system, according to embodiments of the present disclosure.

FIG. 2 is a schematic representation of another exemplary ultrasound communications system 200, consistent with embodiments of the present disclosure. As shown in the example of FIG. 2, system 200 includes a power source 203 and a substrate 201. Power source 203 may include a battery or other power source. Communications system 200 also includes a transducer 207 that generates ultrasound signals. Depending on the layout, geometry, and/or application of system 200, substrate 201 may include one or more electrical connections, including between power source 203 and transducer 207. In the example of FIG. 2, power source 203 is connected to transducer 207 by electrical traces or connections 209*a* and 209*b*. In some embodiments, substrate 201 is a printed circuit board and supports other components in addition to those illustrated in FIG. 2.

Depending on the layout, geometry, and/or application of system 200, transducer 207 may be coupled to substrate 201. In the example of FIG. 2, transducer 207 is coupled directly to substrate 201, either by etching or by embedding. Other forms of coupling are also possible, including mechanical coupling, soldering, etc.

As further shown in the example of FIG. 2, communications system 200 also includes a transistor 205. An environmental variable, for example moisture or temperature, may control the state of transistor 205 and application of power from power source 203 to transducer 207. For example, a moisture or temperature sensor may detect an environmental level and, upon reaching a predetermined level, close transistor 205 to connect power source 203 to transducer 207 via electrical traces or connections 209*a* and 209*b*. As will be appreciated from this disclosure, system 200 may further include other electrical elements, such as capacitors, transistors, transducers, memory, controllers, sensors, switches, etc. (not shown in FIG. 2). Such components may also be coupled to substrate 201 and connected to one another by electrical traces or connections 209*a* and 209*b*.

In some embodiments, transducer 207 may be driven at self-resonance. At self-resonance, the impedance of transducer 105 may be at a minimum because the imaginary portions of the impedance may cancel and the impedance may therefore be equal only to real resistance. Advantageously, this may reduce the power required from power source 203 to drive transducer 207.

In some embodiments, transducer 207 may include a capacitor. Advantageously, the use of a capacitive transducer may reduce the cost of the transducer and/or the system. For example, a surface-mount capacitor may cost approximately ten times less than a Bluetooth® transmitter.

Figure 3:
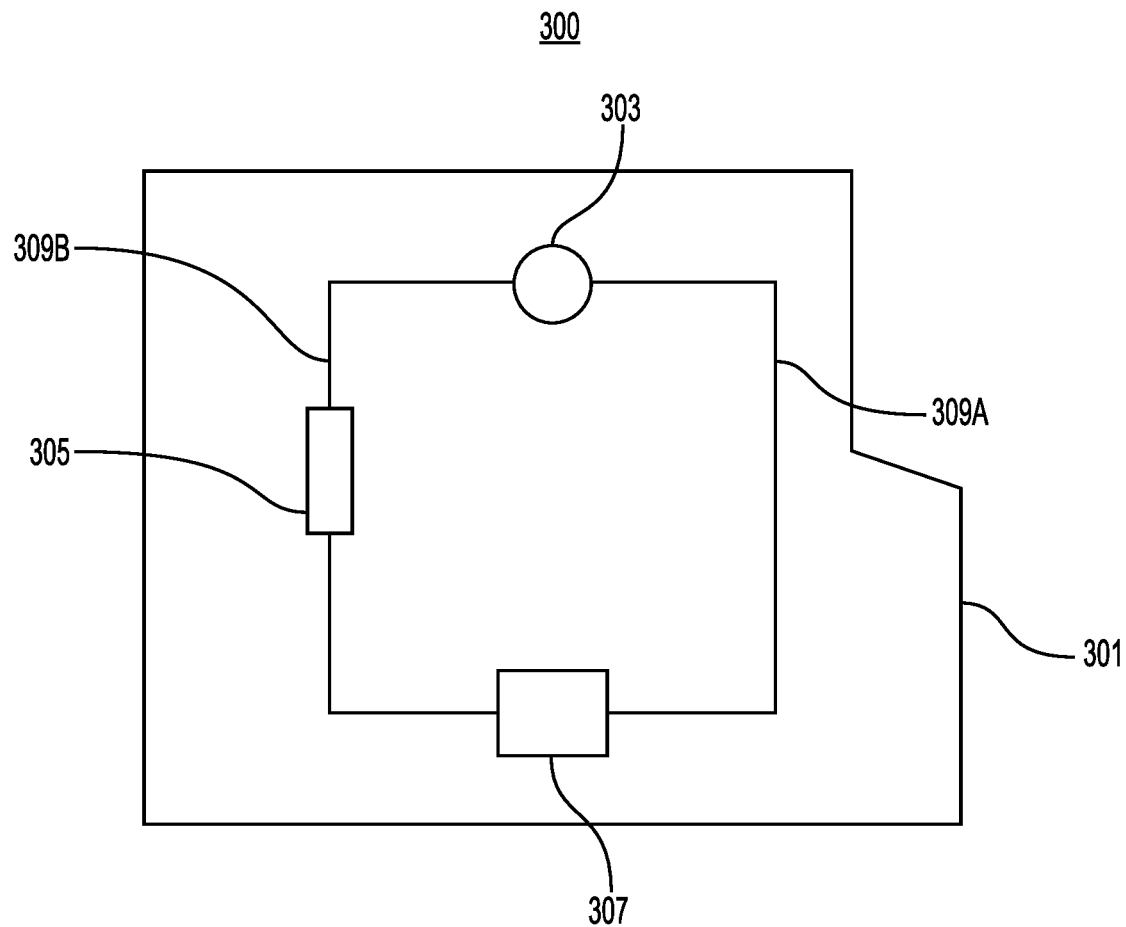
FIG. 3 is a schematic representation of yet another exemplary ultrasound communications system, according to embodiments of the present disclosure.

FIG. 3 is a schematic representation of another exemplary ultrasound communications system 300, consistent with embodiments of the present disclosure. As shown in FIG. 3, communications system 300 includes a power source 303 and a substrate 301. Power source 303 may include a battery or other power source. Communications system 300 includes a transducer 307 that generates ultrasound signals. Depending on the layout, geometry, and/or application of system 300, substrate 301 may include one or more electrical connections, including between power source 303 and transducer 307. In the example of FIG. 3, power source 203 is connected to transducer 307 along electrical traces or connections 309*a* and 309*b*. In some embodiments, substrate 301 is a printed circuit board and supports other components in addition to those illustrated in FIG. 3.

Depending on the layout, geometry, and/or application of communications system 300, transducer 307 may be coupled to substrate 301. In the example of FIG. 3, transducer 307 is coupled directly to substrate 301, either by etching or by embedding. Other forms of coupling are also possible, including mechanical coupling, soldering, etc.

As further shown in FIG. 3, communications system 300 also includes a microcontroller 305. Microcontroller 305 may control power supplied from power source 303 to transducer 307 along electrical traces or connections 309*a* and 309*b*. By way of example, an environmental variable, such as moisture or temperature, may be used by microcontroller 305 to control the application of power from power source 303 to transducer 307. In such cases, a moisture or temperature sensor connected to microcontroller 305 may detect an environmental level and, upon reaching a predetermined level, microcontroller 305 may be activated and cause power to be applied from source 303 to transducer 207 via electrical traces or connections 309*a* and 309*b*. In some embodiments, microcontroller 305 may drive transducer 307 at a resonance frequency using power source 303. For example, microcontroller 305 may include a switch, and power source 303 may include a DC power source, such as a battery. Microcontroller 305 may oscillate the included switch, which may drive transducer 207 with an oscillating current. In some embodiments, microcontroller 305 may contain a processor and a set of instructions, which, when executed by the processor, may control the oscillating current. For example, the processor may increase or decrease the amplitude or frequency of the oscillating current. Advantageously, this may allow transducer 207 to operate at a plurality of frequencies, amplitudes, etc. For example, transducer 207 may operate at a plurality of frequencies corresponding to a plurality of environmental variables or levels.

System 300 may further include other electrical elements, such as capacitors, transistors, transducers, memory, controllers, sensors, switches, etc. (not shown in FIG. 3). Such components may also be coupled to substrate 301 and connected to one another by electrical traces or connections 309a and 309b.

In some embodiments, transducer 307 may be driven at self-resonance. At self-resonance, the impedance of transducer 105 may be at a minimum because the imaginary portions of the impedance may cancel and the impedance may therefore be equal only to real resistance. Advantageously, this may reduce the power required from power source 303 to drive transducer 307.

In some embodiments, transducer 307 may include a capacitor. Advantageously, the use of a capacitive transducer may reduce the cost of the transducer and/or the system. For example, a surface-mount capacitor may cost approximately ten times less than a Bluetooth® transmitter.

Figure 4A:
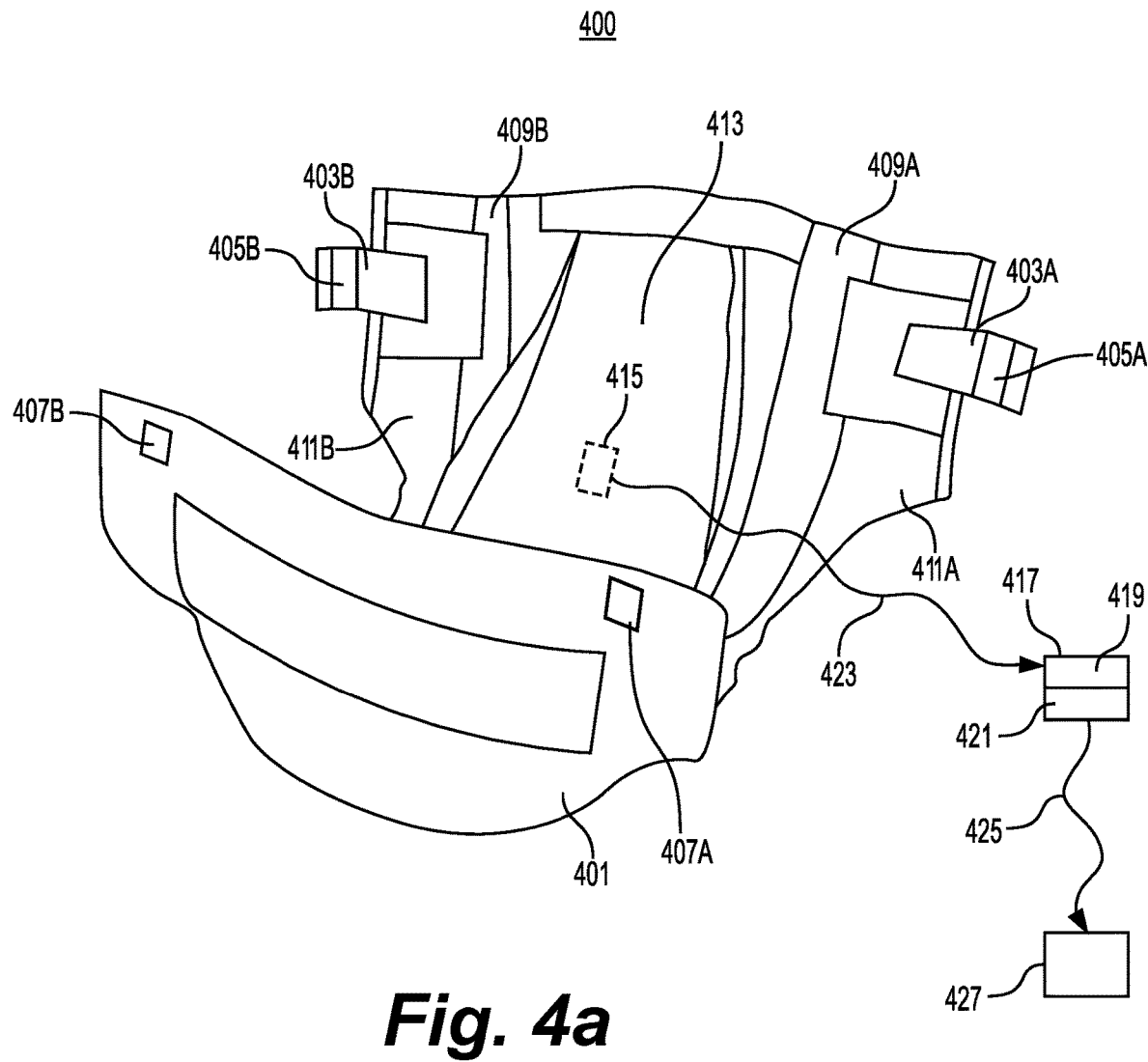
FIG. 4a illustrates an application of the disclosed ultrasound communications system in a diaper.

FIG. 4a illustrates an application of an ultrasound communications system (100, 200, 300, or any combination thereof) in a diaper 400. In the example of FIG. 4a, the diaper 400 may include an outer surface 401, two straps 403a and 403b, two adhesive tabs 405a and 405b, two attachment surfaces 407a and 407b, two guards 409a and 409b, two elastic waists 411a and 411b, and an absorption area 413. The example of FIG. 4a may further include a data transmission system 415. Data transmission system 415 may include an ultrasound communications system (100, 200, 300, or any combination thereof) consistent with the present disclosure and may be embedded in absorption area 413.

In the example of FIG. 4a, data transmission system 415 may activate due to the detected presence of a predetermined level of moisture in absorption area 413. The level of moisture in absorption area 413 may be detected by a sensor of data transmission system 415. In response to detecting the predetermined level of moisture, system 415 may transmit an ultrasound signal 423 indicating the presence of moisture.

In some embodiments, a relay system 417 may be provided to detect the ultrasound signal 423 generated by system 415. Relay system 417 may include one or more detector(s) 419 and one or more repeater(s) 421. Detector 419 may detect the emission of ultrasound signal 423. Detector 419 may convert ultrasound signal 423 to an electrical signal. Repeater 421 may convert the electrical signal into another signal 425, including, for example, an ultrasound signal or an RF signal. Reporting device 427 may detect the emission of signal 425 from relay system 417. Reporting device 427 may notify the user accordingly.

In some embodiments, relay system 417 may be implemented for use as a keychain. In other embodiments, relay system 417 may be implemented as part of user's mobile phone. For example, detector 419 may include a microphone of a conventional mobile phone and repeater 421 may include an RF transmitter of the mobile phone.

As described herein, the reporting of signal 423 to the user through a single relay system 417 as shown in FIG. 4a is used only by way of example. It is possible to use any number of relay systems, as well as any number of detectors and repeaters, in order to increase the range of the signal. It is also possible to convert ultrasound sound 423 to any number of other signals using the one or more relay systems.

Figure 4B:
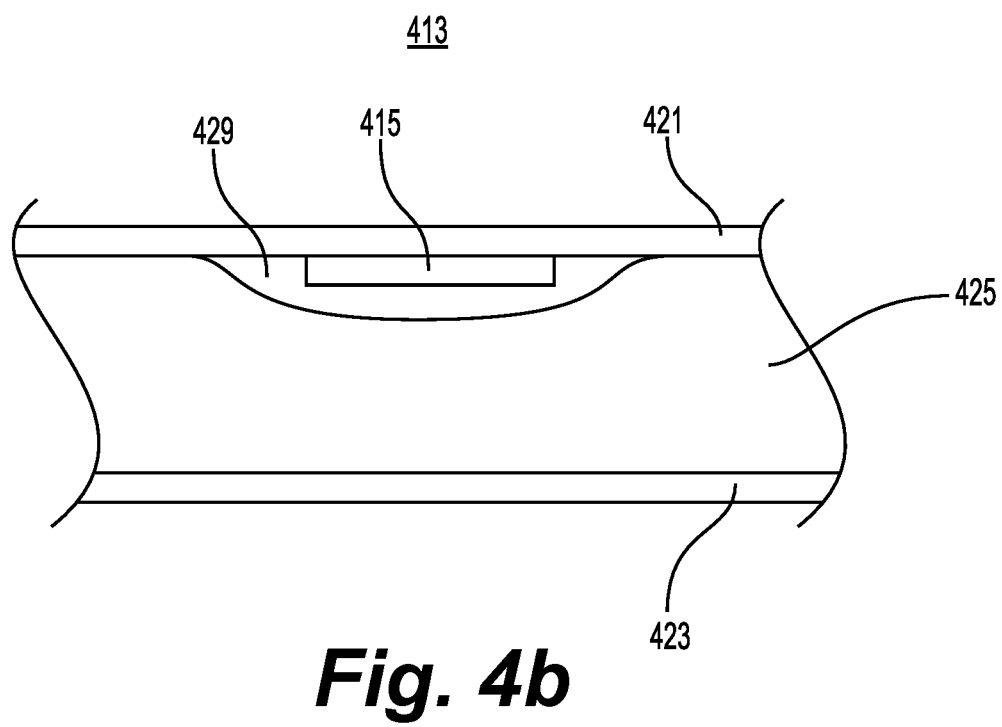

FIG. 4b is a schematic representation of absorption area 413 of FIG. 4a. In the example of FIG. 4b, absorption area 413 may include an upper layer 421, a lower layer 423, and an absorption core 425. Upper layer 421 and lower layer 423 may include, for example, nylon, polyester, polyethylene, polypropylene, or other nonwoven fabrics. Absorption core 425 may include, for example, sodium polyacrylate or other absorbent gels; cellulose acetate or other fibrous material; or any combination thereof. Other embodiments may include additional layers (not shown), such as a topsheet between upper layer 421 and absorption core 425. Such a topsheet may include a hydrophilic material adapted to attract moisture towards absorption core 425.

In some embodiments, data transmission system 415 may include a hard enclosure. In other embodiments, data transmission system 415 may include conformal coating. The coating may include, for example, acrylic, epoxy, polyurethane, silicon rubber, poly-para-xylylene, amorphous fluoropolymer, or other appropriate coatings. In other embodiments, data transmission system 415 may include a soft enclosure.

In the example of FIG. 4b, data transmission system 415 is held between absorption core 425 and upper layer 421 using a pocket 429. In some embodiments, pocket 429 may be attached to upper layer 421 using stitching. In other embodiments, pocket 429 may be attached to upper layer 421 using an adhesive. Preferably, the adhesive may have low toxicity and high moisture resistance and may include, for example, one or more polyolefins.

Positioning data transmission system 415 in place using pocket 429, as shown in FIG. 4b, is disclosed only by way of example. It is possible to hold data transmission system 415 in place in other ways, for example, by using an adhesive. Preferably, the adhesive may have low toxicity and high moisture resistance and may include, for example, one or more polyolefins.

Figure 5:
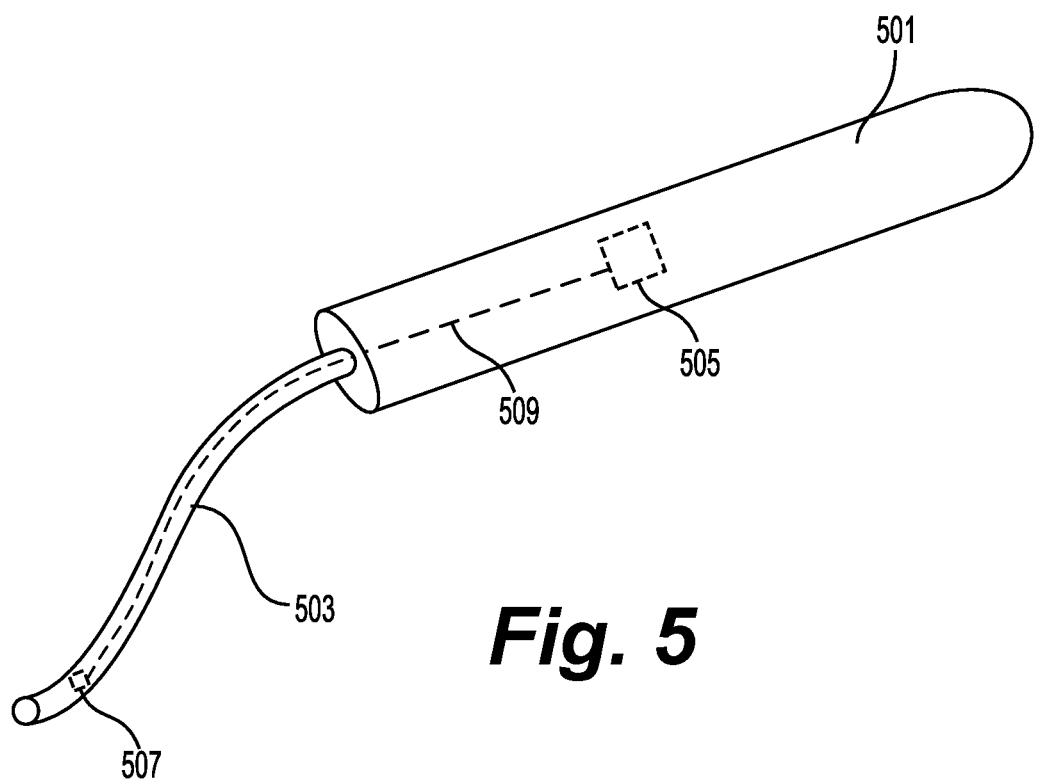
FIG. 5 illustrates another application of the disclosed ultrasound communications system in a tampon.

FIG. 5 is a schematic representation of an application of an ultrasound communications system (100, 200, 300, or any combination thereof) in a tampon 500. In the example of FIG. 5, tampon 500 may include an absorption core 501 and a removal cord 503. The example of FIG. 5 may further include a data transmission system 505. Data transmission system 505 may include an ultrasound communications system (100, 200, 300, or any combination thereof) consistent with the present disclosure and may be embedded in the absorption core 501.

In some embodiments, subsystem 507 may include the transducer and substrate of data transmission system 505 and may be embedded in removal cord 503 and connected to system 505 along electrical connection 509. Advantageously, the signal emitted by the transducer of subsystem 507 may be amplified and/or have an improved transmission range by being located in removal cord 503 as compared to absorption core 501.

Data transmission system 505 may activate due to the detected presence of a predetermined level of moisture in absorption core 501. The level of moisture in absorption core 501 may be detected by a sensor of data transmission system 505. In response to detecting the predetermined level of moisture, system 505 (or subsystem 507) may transmit an ultrasound signal indicating the presence of moisture. A relay system (similar to relay system 417) may be provided to detect and report the ultrasound signal to an external reporting device or monitor.

In the example of FIG. 5, data transmission system 505 is held in the center of absorption core 501 using an adhesive (not shown in FIG. 5). Preferably, the adhesive may have low toxicity and high moisture resistance and may include, for example, one or more polyolefins.

Positioning data transmission system 505 in place using an adhesive, as shown in FIG. 5, is disclosed only by way of example. It is possible to hold data transmission system 505 in place in other ways, for example, by using stitching.

Figure 6:
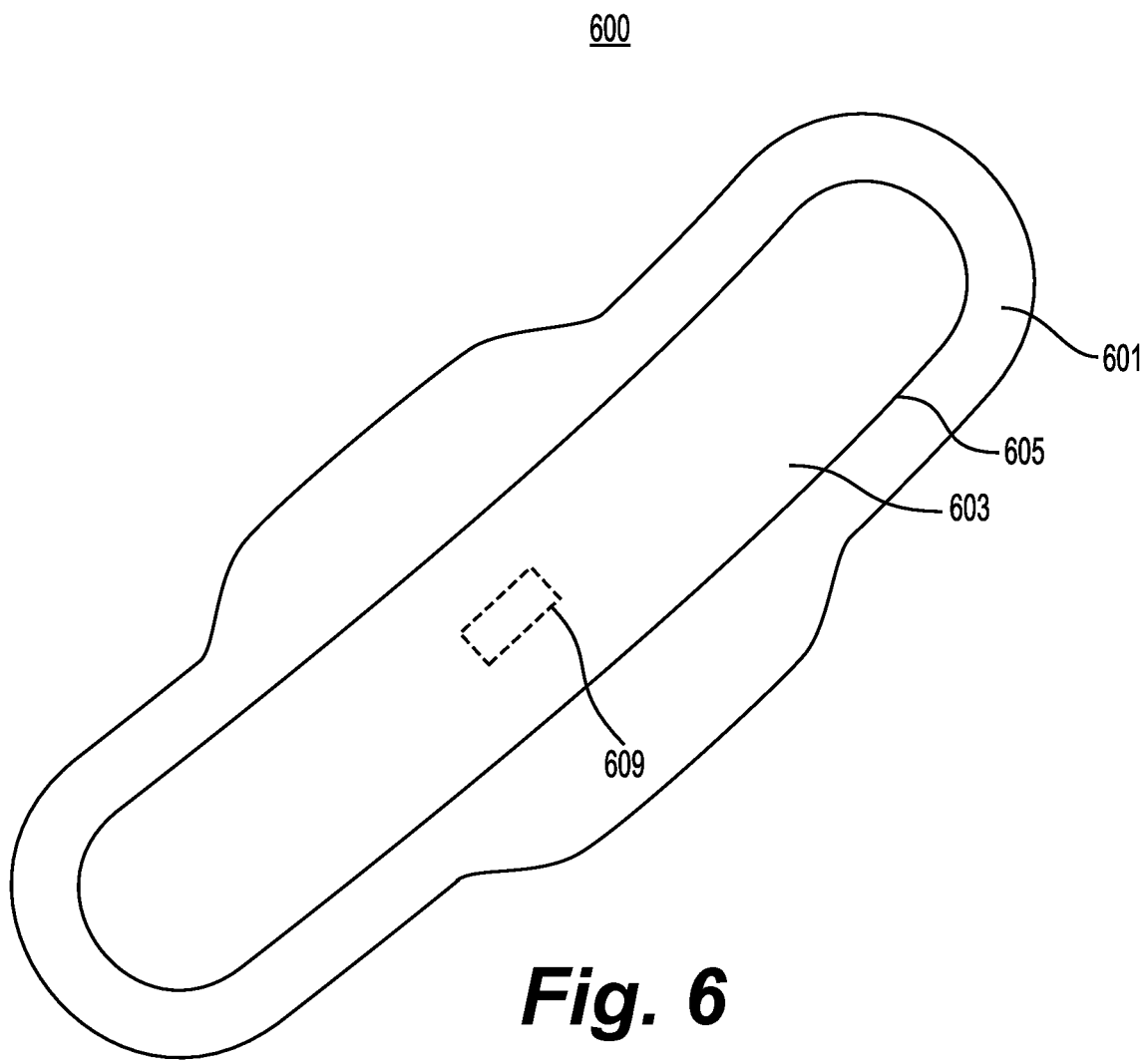
FIG. 6 illustrates yet another application of the disclosed ultrasound communications system in a pad.

FIG. 6 is a schematic representation of an application of an ultrasound communication system (100, 200, 300, or any combination thereof) in a hygiene pad 600. In the example of FIG. 6, hygiene pad 600 may include an absorption core 603 affixed to an outer shell 601 by stitching 605. The example of FIG. 6 may further include a data transmission system 609. Data transmission system 609 may include an ultrasound communications system (100, 200, 300, or any combination thereof) consistent with the present disclosure and may be embedded between absorption core 603 and outer shell 601.

Data transmission system 609 may activate due to the detected presence of a predetermined level of moisture in absorption core 603. The level of moisture in absorption core 603 may be detected by a sensor of data transmission system 609. In response to detecting the predetermined level of moisture, system 609 may transmit an ultrasound signal indicating the presence of moisture. A relay system (similar to relay system 417) may be provided to detect and report the ultrasound signal to an external reporting device or monitor.

In the example of FIG. 6, data transmission system 609 is held between absorption core 603 and outer shell 601 using stitching.

Positioning data transmission system 609 in place using stitching, as shown in FIG. 6, is disclosed only by way of example. It is possible to hold data transmission system 609 in place in other ways, for example, by using an adhesive. Preferably, the adhesive may have low toxicity and high moisture resistance and may include, for example, one or more polyolefins.

Consistent with the present disclosure, other applications of the ultrasound communications system (100, 200, 300, or any combination thereof) may be implemented beyond the examples provided in FIGS. 4-6. This includes biosensor applications for other types of personal hygiene products, as well as other applications where a low power and cost efficient, ultrasound communications system may be advantageously used in place of other conventional solutions. This includes applications for disposable products and miniaturized devices.

Figure 7:
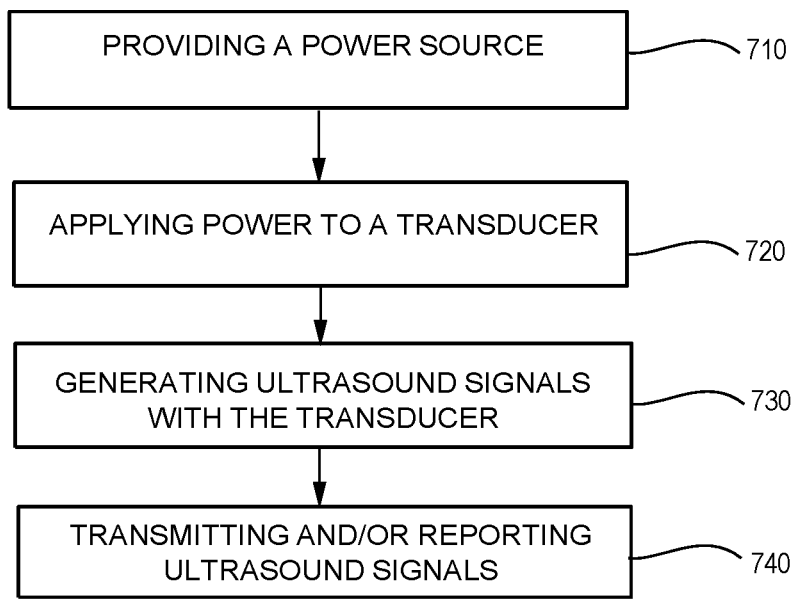
FIG. 7 is flowchart of an exemplary method for transmitting data with an ultrasound transducer, according to embodiments of the present disclosure.

FIG. 7 is a flowchart of an exemplary method for transmitting data using an ultrasound communications system, such as systems 100, 200, 300, or any combination thereof. The various features and advantages of systems 100, 200, and 300 are described above with reference to FIGS. 1-3.

At step 710 in FIG. 7, a power source such as power source 103, 203, or 303 is provided. As described above, the power source may be a battery or other suitable power source. Depending on the application, the power source may be activated upon detection of a predetermined condition. For example, in the case of a biosensor application for a personal hygiene product, the predetermined condition may be a detected level of moisture or temperature. To activate the power source, a transistor or switch may be closed so that power can be supplied from the power source. In other embodiments, a controller is powered by the power source and may control the supply of power to other components (such as a transducer) when a predetermined condition is detected or determined to be met.

At step 720, a transducer such as transducer 105, 207, or 307 receives power from the power source. In some embodiments, the transducer may be electrically connected to the power source using electrical traces or connections. As described above, the supply of power to the transducer may be controlled or regulated by a switch, transistor, or controller. At step 730, the transducer generates ultrasound signals in response to receiving power from the power source. In some embodiments, the transducer may be coupled to a substrate that functions as a soundboard to resonant and amplify the ultrasound signals. At step 740, the ultrasound signals are transmitter and, optionally, an external reporting device receives the ultrasound signals or converted signals thereof. To facilitate the transmission of the ultrasound signals, a substrate may be coupled to the transducer and function as a soundboard, as disclosed herein. The reporting device may be a monitor or similar device for reporting the signal or presence of the predetermined condition (e.g., a moisture level) to a user.

The example method 700 may include additional steps. For example, in some embodiments, method 700 may include activating a switch or transistor such as transistor 205 to cause power to be applied to the transducer from the power source. In other embodiments, method 700 may include causing a controller or microcontroller 305 to control power supplied to the transducer from the power source.

In some embodiments, method 700 may include relaying the ultrasound signals generated by the transducer to an external reporting device using a relay system that includes one or more detectors and one or more repeaters. As described above, a relay system may extend the transmission range of the ultrasound transducer.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A data transmission system, comprising:
   an ultrasound transducer configured to generate ultrasound signals in response to power supplied from a power source; and
   a mechanical ultrasound amplifier coupled to the ultrasound transducer, the ultrasound amplifier comprising a substrate adapted to function as a soundboard to amplify the ultrasound signals.

2. The data transmission system of claim 1, wherein the substrate comprises a printed circuit board, and one or more solder pads couple the ultrasound transducer to the printed circuit board.

3. The data transmission system of claim 1, wherein the ultrasound transducer includes a capacitor.

4. The data transmission system of claim 1, wherein the ultrasound transducer has a resonant frequency.

5. The data transmission system of claim 4, wherein the substrate is configured to have substantially the same resonant frequency as the ultrasound transducer.

6. The data transmission system of claim 1, further comprising:
   at least one of a detector or a repeater adapted to receive the ultrasound signals and re-transmit the received ultrasound signals.

7. A data transmission system for use in a personal hygiene product, comprising:
   a moisture sensor coupled to the personal hygiene product;
   an ultrasound transducer configured to generate ultrasound signals in response to power supplied from a power source; and
   a mechanical ultrasound amplifier coupled to the ultrasound transducer, the ultrasound amplifier comprising a substrate adapted to function as a soundboard to amplify the ultrasound signals.

8. The data transmission system of claim 7, where the personal hygiene product comprises one or more of a diaper, liner, pad, or tampon.

9. The data transmission system of claim 7, wherein the substrate comprises a printed circuit board, and one or more solder pads couple the ultrasound transducer to the printed circuit board.

10. The data transmission system of claim 7, wherein the ultrasound transducer has a resonant frequency.

11. The data transmission system of claim 7, wherein the substrate is configured to have substantially the same resonant frequency as the ultrasound transducer.

12. The data transmission system of claim 7, further comprising:
    at least one of a detector or a repeater adapted to receive the ultrasound signals and re-transmit the received ultrasound signals.

13. A data transmission method, comprising:
    applying power from a power source to an ultrasound transducer, the ultrasound transducer physically coupled to a substrate and electrically coupled to the power source, the substrate adapted to function as a soundboard to amplify ultrasound signals generated by the ultrasound transducer;
    in response to the ultrasound transducer receiving the power from the power source, generating ultrasound signals with the ultrasound transducer; and
    amplifying the ultrasound signals using the substrate, the substrate functioning as a soundboard for the ultrasound transducer.

14. The method of claim 13, wherein applying power to the ultrasound transducer comprises:
    detecting an environmental level with a sensor; and
    controlling power supplied from the power source to the ultrasound transducer in response to detecting the environmental level with the sensor.

15. The method of claim 14, wherein the environmental level is at least one of a moisture level or a temperature level.

16. The method of claim 14, wherein the sensor is located in an absorption area of a personal hygiene product.

17. The method of claim 13, further comprising:
    relaying, using a relay device, the ultrasound signals to an external reporting device, the relay device including at least one of a detector or a repeater.

18. The method of claim 13, wherein the substrate comprises a printed circuit board, and the ultrasound transducer is coupled to the printed circuit board using one or more solder pads.

19. The method of claim 13, wherein the ultrasound transducer has a resonant frequency, and wherein the ultrasound transducer is driven at the resonant frequency.

20. The method of claim 19, wherein the substrate has a resonant frequency substantially having substantially the same resonant frequency as the ultrasound transducer's resonant frequency.

* * * * *